(12) United States Patent
Cioli

(10) Patent No.: US 6,300,358 B1
(45) Date of Patent: *Oct. 9, 2001

(54) USE OF BENZYDAMINE IN THE TREATMENT OF PATHOLOGICAL CONDITIONS CAUSED BY TNF

(75) Inventor: Valerio Cioli, Roma (IT)

(73) Assignee: Angelini Ricerche S.p.A. Societa'Consortile, S. Palomba-Pomezia (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/586,804

(22) PCT Filed: Jul. 14, 1994

(86) PCT No.: PCT/EP94/02343

§ 371 Date: May 6, 1996

§ 102(e) Date: May 6, 1996

(87) PCT Pub. No.: WO95/03799

PCT Pub. Date: Feb. 9, 1995

(30) Foreign Application Priority Data

Jul. 27, 1993 (IT) .............................................. MI93A1673

(51) Int. Cl.$^7$ ................................................. A61K 31/415
(52) U.S. Cl. ............................................ 514/394; 514/393
(58) Field of Search ............................................ 514/394

(56) References Cited

U.S. PATENT DOCUMENTS 4,980,160 * 12/1990 Goldberg et al. ................... 424/85.1
5,563,143 * 10/1996 Cohan et al. ........................ 514/216

OTHER PUBLICATIONS

Fahey et al., "Status of immne–based therapies in HIV infection and AIDS", Clin. exp. Immunol. 88, 1–5, 1992.*
Stedman's Medical Dictionary, 24th Edition, p. 931, col. 2, the last entry, Feb. 24, 1983.*
Editor–in–Chief Jay Stein, Chapters 71 and 72, pp. 699–715, 1994.*
Gilman et al., Goodman and Gilman's The Pharmacological Basis of Therapeutics, 6th Edition, Apr., 1981, pp. 682–687.*
Brennan et al., Lacet, 2, pp. 244–277, 1989, (see Background of Cohan et al.).*
Fiers, W., FEBS Letters, 1991, 285, p. 199, (see Background of Cohan et al.).*
Spooner, C. E., et al., Clinical Immunology and Immunopathology, 1992, 62, p. S11, (see Background of Cohan et al.).*
Herdman et al. Clinical Otolaryngol. Allied Sci., vol. 14, No. 4, pp. 323–332, 1989.*
DiPiro et al., Pharmacotherapy, A Pathophysiologic Approach, pp. 1259–1264, 1989.*
Matsumiya, The Japanese Journal of Tuberculosis and Chest Diseases, vol. 19, Nos. 1–2, pp. 17–32, Apr. 1975.*

* cited by examiner

Primary Examiner—Dwayne C. Jones
(74) Attorney, Agent, or Firm—Oblon, Spivak, McClelland, Maier & Neustadt, P.C.

(57) ABSTRACT

Use of benzydamine and physiologically acceptable acid addition salts thereof for preparing a medicament for the treatment of pathological conditions caused by TNF.

11 Claims, No Drawings

USE OF BENZYDAMINE IN THE TREATMENT OF PATHOLOGICAL CONDITIONS CAUSED BY TNF

This application is a 371 of PCT/EP94/02343, filed on Jul. 14, 1994.

BACKGROUND OF THE INVENTION

The present invention relates to the use of benzydamine and physiologically acceptable acid addition salts thereof in the treatment of pathological conditions caused by TNF (Tumour Necrosis Factor).

Benzydamine (The Merck Index, 9th ed., 1976, page 147 no. 1136) was described for the first time in the patent U.S. Pat. No. 3,318,905 which relates to a group of substances having analgesic, anti-inflammatory and muscle relaxant activity.

Benzydamine has been widely used in practice in human treatment as hydrochloride salt. By the systemic route it is mainly used as an antiphlogistic and analgesic. Topically it is however mainly used for those diseases which involve local inflammation such as for example myalgia, tendinitis, vulvovaginitis, gingivitis, stomatitis, mucositis of the oral cavity and so forth.

Moreover benzydamine salicylate has been used in rheumatic disorders.

TNF is a non-glycosylated polypeptide having relative molecular mass ($M_r$) of 17,500 (17.5 KDa) and known amino acid sequence, and it is supposed that the active form is trimeric (Old L. J. "Science", 1985, 230, 630–632; Beutler B. et al. "Nature", 1986, 320, 585–588; Jones E. Y. et al. "Nature", 1989, 338, 225–228; Corti A. et al. "Biochem. J., 1992, 284, 905–910).

TNF, also known as alpha TNF or cachectin belongs to the family of cytokines and as such plays a part in the stimulation of immune responses to defend the organism from external attacks (Epstein F. H. "The New England J. of Med.", 1987, 316, 379–385; Urdal D. L. "Annual Reports in Med. Chem.", 1991, 26, 221–227).

On the other hand, an excessive action by TNF may in itself become an actual pathogenetic cause given the considerable toxicity of TNF (Waage A. et al. "Immunological Reviews", 1992, No. 127, 221–230).

It is thus acknowledged that TNF plays a very important role in some very serious pathological conditions of an acute and chronic nature such as, for example, septic shock and cachexia (Epstein F. H., loc. cit.; Waage A. et al., loc. cit.) and multiple sclerosis (Dijkstra D. C. et al., Trends in Pharm. Sc., 14, 124–129, 1993).

Therefore, while for many years researches about TNF have aimed at studying its properties, structure and preparation, in recent years the need has been felt for agents capable of interfering with the production or action of TNF, to be used as therapeutical means in pathologies wherein toxic, bacterial, viral or endogenous agents lead, by stimulating the macrophages, to the production of toxic concentrations of TNF.

Thus compounds capable of interfering with TNF, albeit by different mechanisms, have been identified.

More particularly, it has been reported that some compounds are capable of protecting some particularly sensitive cell lines from the toxic action of TNF.

Suramin (EP-A-0 486 809), thalidomide (Sampaio E. P. "J. Exp. Med.", 173, 699–703, 1991) and some derivatives of glutarimides such as cyclohexymide ("Transplant Proc." 23, 254–5, 1991) interfere, albeit in different ways and with different specificity, in the production of TNF.

In contrast, vinigrol (PCT-WO-91/07953; Weber E. "J. Org. Chem." 52, 5292–5293, 1987) interferes with the action of TNF without altering its synthesis.

Before an antagonistic action in respect of TNF had been identified, there was no connection between these compounds either as far as regards their structure or clinical use.

In fact suramin, i.e. 8,8'-(carbonylbis(imino-3,1-phenylene carbonylimino (4-methyl-3,1-phenylene) carbonylimino)) bis-1,3,5-naphthalene trisulfonic acid, was known as trypanocide. Cyclohexymide, i.e. 4-(2-(3,5-dimethyl-2-oxo-cyclohexyl)-2-hydroxyethyl)-2,6-piperidindione was known as fungicide. Vinigrol, i.e. 4,8a (1H)-diol,4,4a,5,6,7,8-hexahydro-3-(hydroxymethyl)-8,9-dimethyl-12-(1-methylethyl)-(1R-1alpha, 4beta, 4alpha beta, 5alpha, 8beta, 8alpha beta, 9S*, 12S*))-1,5-butanonaphthalene was known as an hypotensive and an anti-platelet aggregant.

Finally, experiments performed by the Applicant have shown that conventional anti-inflammatory agents such as ibuprofen and indomethacin do not antagonise TNF (see Example 1).

SUMMARY OF THE INVENTION

Unexpectedly it has now been found that benzydamine and physiologically acceptable acid addition salts thereof protect, in vitro, cultures of sensitive cells from the toxic action of TNF and antagonize, in vivo, the oedema-forming action of TNF on rat paw.

The experiments carried out to date show that the action of benzydamine and physiologically acceptable acid addition salts thereof is performed, in respect of TNF, at dosages higher than those administered to achieve an anti-inflammatory effect.

Therefore it is a first object of the present invention to use benzydamine and physiologically acceptable acid addition salts thereof for preparing a drug for the treatment of pathological conditions caused by TNF.

Typical examples of the pathological conditions caused by TNF are: septic shock, cachexia, i.e the general debilitation which accompanies neoplastic diseases (Balkwill F. et al. "The Lancet", ii Sec., 1229–12232, 1987), chronic viral or bacterial infections such as tuberculosis or AIDS (Barnes P.F. et al. "The Journal of Immunology", 145, 149–154, 1990) or degenerative diseases such as multiple sclerosis (Dijkstra et al., loc. cit.) or ulcerative colitis.

A second object of the present invention is to provide a therapeutical method of treatment comprising administering an effective amount of benzydamine or of a physiologically acceptable acid addition salt thereof to a patient suffering from a pathological condition caused by TNF.

DESCRIPTION OF THE PREFERRED EMBODIMENTS

For practical applications the compounds of the present invention can be administered as they are, but they are preferably administered in the form of pharmaceutical preparations for systemic use.

The pharmaceutical preparations of the present invention may be administered by systemic or topical route.

When used by systemic route, they may be solid, like tablets, dragees, capsules, powders and slow-release forms or liquid, such as sterile solutions for intramuscular or intravenous injections, suspensions and emulsions.

The pharmaceutical preparations for topical use may be vaginal dosage forms like solutions for lavages, creams and foams, dosage forms for treating the buccal cavity like mouth washings and sprays, as well as dosage forms for the nose and the ear such as ointments, pastes, creams, foams, gels, solutions and powders.

In addition to conventional excipients, the preparations of the present invention may comprise other suitable pharmaceutical additives such as preservatives, stabilisers, emulsifiers, salts for regulating osmotic pressure, buffers, colouring and flavouring agents.

When required by particular therapies, the preparations of the present invention may also comprise other compatible active ingredients whose simultaneous administration is helpful.

For practical uses in therapy the effective amount of benzydamine and of the physiologically acceptable acid addition salts thereof may vary over a rather broad range depending on known factors, such as the specific treatment required, the selected pharmaceutical preparation and the administration route. However, the optimum effective amount can easily be accomplished by the physician concerned according to simple routine procedures.

In general, the daily dosage will preferably range from 0.1 to 10 mg/kg or, even more preferably, from 3 to 10 mg/kg of benzydamine base. Of course, in the case of an acid addition salt thereof, an amount corresponding to the above-mentioned amount of benzydamine base will be administered.

The pharmaceutical preparations of the present invention can be made following the conventional techniques of the pharmaceutical chemist involving mixing, granulating and compressing when necessary, or variously mixing and dissolving the ingredients as appropriate to give the desired result.

The following examples are intended to illustrate the present invention without, however, limiting it.

EXAMPLE 1

Effect of benzydamine, ibuprofen and indomethacin on the toxicity of TNF in vitro Cell cultures L929 were incubated with TNF (murine recombinant alpha-TNF "Genzyme") with or without the addition of benzydamine hydrochloride, ibuprofen and indomethacin at a dose of 31 $\mu$g/ml according to D. R. Branch et al. (J. of Immunological Methods 143, 251–261 (1991)).

Optical density of the solutions provides a direct determination of the number of surviving cells and is measured by using Titertek MKII equipped with a 550 nm filter. The results are shown in Table 1.

TABLE 1

|  | OPTICAL DENSITY (ABS) |
| --- | --- |
| Control | 0.768 |
| TNF (1 $\mu$/ml) | 0.133 |
| TNF + ibuprofen | 0.118 |
| TNF + indomethacin | 0.152 |
| TNF + benzydamine | 0.573 |

EXAMPLE 2

Effect of benzydamine in tissue lesion caused by TNF in rat

This test was carried out on three groups of 5 rats each (males, CD breed, weight 101–125 g). Oedema was induced by injecting 40,000 units (0.1 ml) of a commercial TNF solution (murine recombinant alpha-TNF "Genzyme") into the rear right paw.

In the rats of the second group (group B), a solution of benzydamine hydrochloride was also injected, simultaneously, at a dose of 40 mg/kg subcutaneously, while in the rats of the third group (group C) indomethacin was administered orally at a dose of 3 mg/kg. The volume of the paw was measured, at the times given in the table, with a BASILE plethysmometer according to C. A. Winter et al. in "Proceedings of the Society for Experimental Biology and Medicine Vol. III, 544–547, 1962".

The results are shown in Table 2.

TABLE 2

Effect of benzydamine on tissue lesion caused by TNF in rat

| Group | paw volume variation (mL) over time | | | | |
| --- | --- | --- | --- | --- | --- |
|  | 0 | 30' | 1h | 3h | 6h |
| A | 0 | +90 | +70 | +90 | +10 |
| B | 0 | +50 | +30 | +30 | −10 |
| C | 0 | +110 | +40 | +90 | +110 |

Group A is the control group, group B is the one treated with benzydamine and group C is the one treated with indomethacin. The significance of the data is p <0.01.

What is claimed is:

1. A method of treating a pathological condition caused by tumor necrosis factor, comprising administering to a patient in need thereof an effective amount of benzydamine or a physiologically acceptable acid addition salt thereof.

2. The method of claim 1, wherein said pathological condition is selected from the group consisting of septic shock, cachexia, general debilitation accompanying neoplastic disease, chronic viral infection, chronic bacterial infection and degenerative diseases.

3. The method of claim 1, wherein said pathological condition is a bacterial infection and said bacterial infection is tuberculosis.

4. The method of claim 1, wherein said pathological condition is a viral infection and said viral infection is an AIDS viral infection.

5. The method of claim 1, wherein said pathological condition is a degenerative disease and said degenerative disease is multiple sclerosis or ulcerative colitis.

6. The method of claim 1, wherein said effective amount is 0.1 to 10 mg/kg per day as benzydamine base.

7. The method of claim 6, wherein said effective amount is 3 to 10 mg/kg per day as benzydamine base.

8. A method of inhibiting the action of Tumor Necrosis Factor on cells, comprising contacting affected cells with an effective amount of benzydamine.

9. The method of claim 1 wherein said pathological condition is septic shock.

10. The method of claim 1 wherein said pathological condition is chronic viral infection.

11. The method of claim 1 wherein said pathological condition is the general debilitation accompanying neoplastic disease.

* * * * *